US010598645B2

(12) United States Patent
Kao et al.

(10) Patent No.: US 10,598,645 B2
(45) Date of Patent: Mar. 24, 2020

(54) TESTING SYSTEM AND METHOD FOR AIR SENSING DEVICE

(71) Applicant: DELTA ELECTRONICS, INC., Taoyuan (TW)

(72) Inventors: Ming Kao, Taoyuan (TW); Yuan-Ping Hsieh, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 203 days.

(21) Appl. No.: 15/681,138

(22) Filed: Aug. 18, 2017

(65) Prior Publication Data
US 2018/0335409 A1    Nov. 22, 2018

(30) Foreign Application Priority Data

May 17, 2017 (TW) .............................. 106116252 A (51) Int. Cl.
*G01N 33/00* (2006.01)
*G01N 15/06* (2006.01)
*G01N 1/22* (2006.01)

(52) U.S. Cl.
CPC ......... *G01N 33/0006* (2013.01); *G01N 15/06* (2013.01); *G01N 33/0016* (2013.01); *G01N 33/0047* (2013.01); *G01N 1/2273* (2013.01)

(58) Field of Classification Search
None
See application file for complete search history.

(56) References Cited

U.S. PATENT DOCUMENTS

| 5,255,556 A * | 10/1993 | Lobdell ................ G01N 1/2273 340/602 |
| 5,644,070 A * | 7/1997 | Gibboney ................ A61L 2/202 422/186.08 |
| 6,282,940 B1 * | 9/2001 | Hung .................... G01N 33/004 73/1.06 |
| 8,980,172 B1 * | 3/2015 | Resch ................ G01N 33/0031 422/5 |

(Continued)

FOREIGN PATENT DOCUMENTS

| CN | 204855490 | 12/2015 |
| CN | 106645572 | 5/2017 |
| TW | 201713903 | 4/2017 |

OTHER PUBLICATIONS

Office Action dated Apr. 30, 2018 from corresponding application No. TW 106116252.

*Primary Examiner* — Peter J Macchiarolo
*Assistant Examiner* — Mohammed E Keramet-Amircolai
(74) *Attorney, Agent, or Firm* — Hauptman Ham, LLP (57) ABSTRACT

A testing system used for an air sensing device is disclosed, the testing system includes a controller, a vacuum test cabinet, a molecule generator, a vacuum pump, a VOC sensor, a carbon dioxide sensor, a temperature sensor, a humidity sensor, and a heater. The vacuum test cabinet accommodates the air sensing device to be tested. The controller controls the vacuum pump to extract air from the vacuum test cabinet so as to create a predetermined vacuum level. The controller controls the molecule generator to generate a quantitative gas and transmits the quantitative gas to the vacuum test cabinet. The controller obtains a system value of gas data. The controller obtains a measure value of the gas data of the air sensing device and compares the measure value with the system value to determine whether the air sensing device senses correctly.

17 Claims, 5 Drawing Sheets

(56) References Cited

U.S. PATENT DOCUMENTS

| | | | |
|---|---|---|---|
| 2004/0179970 A1* | 9/2004 | Matsubara | G01N 27/125 422/90 |
| 2004/0197092 A1* | 10/2004 | Koch | G01N 33/007 392/399 |
| 2005/0145493 A1* | 7/2005 | Saffell | G01N 27/4045 204/431 |
| 2006/0236752 A1* | 10/2006 | Nakamura | G01N 33/0032 73/23.21 |
| 2006/0266096 A1* | 11/2006 | Eickhoff | G01N 27/4163 73/1.06 |
| 2008/0159914 A1* | 7/2008 | Ohashi | G01N 33/493 422/68.1 |
| 2008/0282765 A1* | 11/2008 | Bonne | G01N 33/0006 73/1.07 |
| 2010/0289655 A1* | 11/2010 | Elrod | G01N 33/0039 340/632 |
| 2011/0108418 A1* | 5/2011 | Nauber | G01N 33/007 204/409 |
| 2012/0048748 A1* | 3/2012 | Wickersham, Jr. | G01N 15/0656 205/789 |
| 2012/0249293 A1* | 10/2012 | Chen | G07C 9/00158 340/5.52 |
| 2013/0186776 A1* | 7/2013 | Scheffler | G01N 27/26 205/785.5 |
| 2013/0300663 A1* | 11/2013 | Gu | G06F 3/033 345/166 |
| 2013/0300713 A1* | 11/2013 | Gu | G06F 1/3259 345/175 |
| 2013/0335346 A1* | 12/2013 | Chen | G06F 3/041 345/173 |
| 2013/0342443 A1* | 12/2013 | Huang | G06F 3/017 345/156 |
| 2015/0153785 A1* | 6/2015 | Kao | G06F 1/1681 361/679.55 |
| 2015/0260698 A1* | 9/2015 | Hirata | G01M 15/102 73/23.31 |
| 2015/0263123 A1* | 9/2015 | Cheng | H01L 29/66825 257/319 |
| 2016/0007929 A1* | 1/2016 | Chuang | A61B 5/02427 600/324 |
| 2016/0012656 A1* | 1/2016 | Chuang | G07C 9/00071 340/5.52 |
| 2016/0063833 A1* | 3/2016 | Schultz | G08B 19/00 340/522 |
| 2016/0363582 A1* | 12/2016 | Blackley | G01N 33/497 |
| 2017/0106218 A1 | 4/2017 | Lin et al. | |
| 2017/0146501 A1* | 5/2017 | Martens | G01N 33/007 |

\* cited by examiner

TESTING SYSTEM AND METHOD FOR AIR SENSING DEVICE

BACKGROUND OF THE INVENTION

Field of the Invention

The present invention relates to a testing system, and especially to a testing system and a method for an air sensing device.

Description of Prior Art

A traditional air sensing product, such as an air purifier, draws standard gas from cavity cover thereof to perform measuring by an air concentration detector in order to determine whether the air concentration detector detects correctly. The method further controls temperature and humidity, and a gas distribution mechanism is used for the preparation of standard concentration gas and background gas, and test gas with standard concentration, arranged and stored in test chamber, is used for testing sensitivity of sensor sensing test gas under standard concentration. Moreover, a gas mass flow control, on-off control of each pneumatic solenoid valve, start-stop control of pumps, start-stop control of stirring fans, and test process control of the measured sensor is included.

The aforementioned testing system may make the sensor quickly sense the standard gas by an automatic arrangement of the standard gas. Synchronous test of multi-sensor electrical gas response and single sensor optical gas response may also be implemented. However, the testing system mentioned above does not include functions of qualitative or quantitative evaluation, automatic test, automatic determination, and so on.

However, the conventional air sensor is only used for sensing the air medium without qualitative or quantitative evolution for testing so that testing results of the qualitative or quantitative evolution may tend to be incorrect.

SUMMARY OF THE INVENTION

Accordingly, the present invention provides a testing system for an air sensing device having a gas sensor to overcome the drawbacks of the traditional testing system, and achieve functions of qualitative and quantitative evaluations, automatic tests, and automatic determinations. The testing system includes a controller, a vacuum test cabinet, a molecule generator, a vacuum pump, a VOC sensor, a carbon dioxide sensor, a temperature sensor, a humidity sensor, and a heater. The vacuum test cabinet accommodates the air sensing device. The vacuum pump is connected to the vacuum test cabinet and the controller. The molecule generator is connected to the vacuum test cabinet and the controller. The controller controls the vacuum pump to extract air from the vacuum test cabinet so as to create a predetermined vacuum level. The controller controls the molecule generator to generate a quantitative gas and transmits the quantitative gas into the vacuum test cabinet. The controller obtains a system value of gas data. The controller obtains a measure value of the gas data of the gas sensor of the air sensing device and compares the measure value of the gas data with the system value of the gas data for determining whether the gas sensor senses correctly, and further modifying a sensing value.

Besides, the present invention further provides a testing method for an air sensing device having a gas sensor. The testing method includes the following steps: (a) arranging at least one air sensing device in a vacuum test cabinet; (b) controlling a vacuum pump by the controller to extract air from the vacuum test cabinet for creating a predetermined vacuum level; (c) controlling a molecule generator by the controller to generate a quantitative gas and transmit the quantitative gas into the vacuum test cabinet for the controller obtaining a system value of gas data; and (d) obtaining a measure value of the gas data of the gas sensor of the air sensing device and comparing the measure value of the gas data with the system value of the gas data by the controller for determining whether the gas sensor senses correctly.

BRIEF DESCRIPTION OF DRAWING

One or more embodiments of the present invention are illustrated by way of example and not limitation in the figures of the accompanying drawings, in which like references indicate similar elements. These drawings are not necessarily drawn to scale.

DETAILED DESCRIPTION OF THE INVENTION

Figure 1:
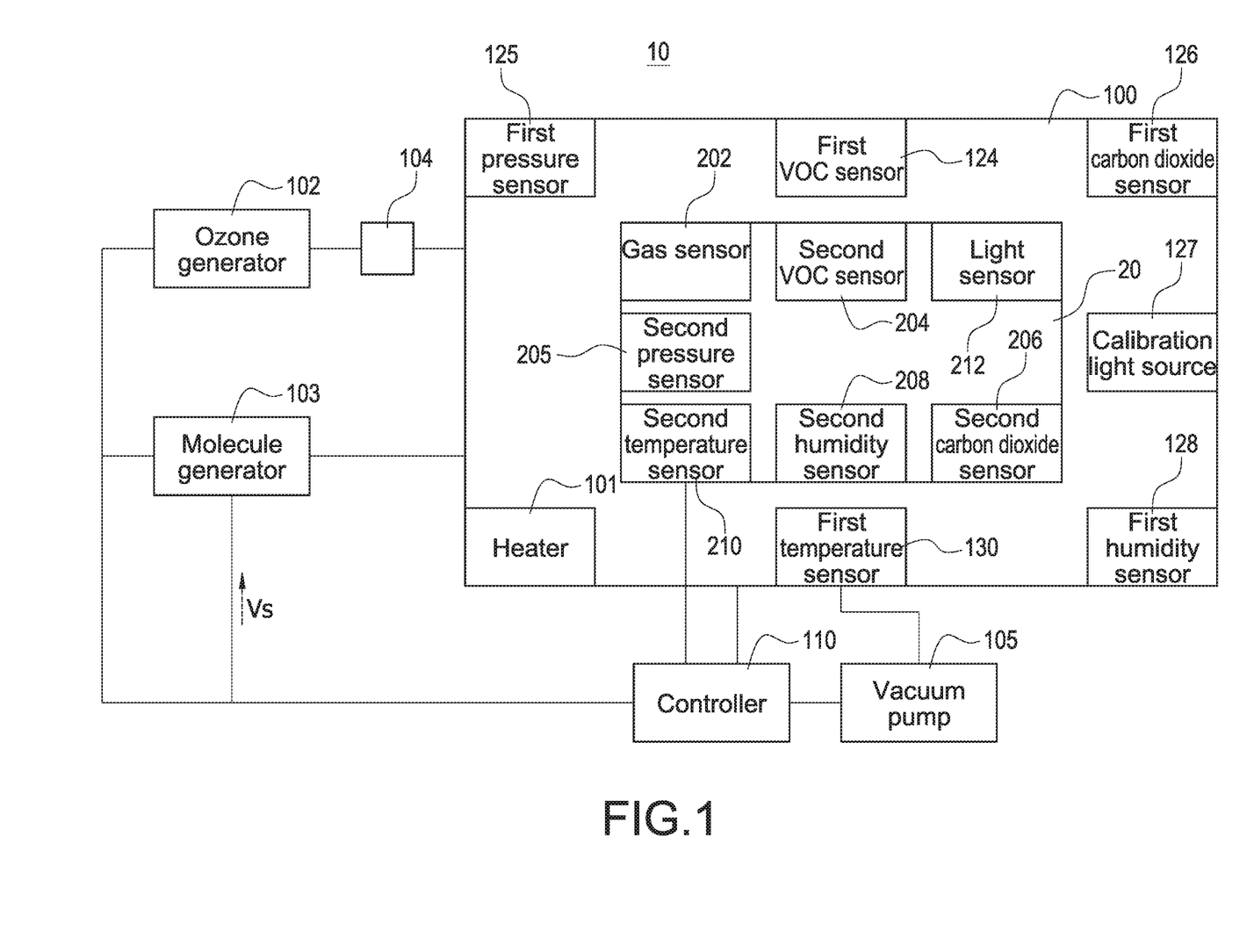
FIG. 1 is a block diagram of a testing system for an air sensing device according to an embodiment of the present invention.

Please refer to FIG. 1, which shows a block diagram of a testing system for an air sensing device (hereafter referred to as "testing system 10") according to an embodiment of the present invention. The testing system 10 includes a vacuum test cabinet 100, a vacuum pump 105, an ozone generator 102, a molecule generator 103, and a controller 110. The vacuum test cabinet 100 includes at least one heater 101 for accommodating device(s) 20 to be tested (such as accommodating multiple devices 20 to be tested). The vacuum pump 105 is connected to the vacuum test cabinet 100. The ozone generator 102 is connected to the vacuum test cabinet 100. The molecule generator 103 is connected to the vacuum test cabinet 100. The controller 110 is connected to the vacuum test cabinet 100, the vacuum pump 105, the ozone generator 102, and the molecule generator 103. Moreover, the ozone generator 102 is connected to the vacuum test cabinet 100 via a linear valve 104, while the molecule generator 103 is connected directly to the vacuum test cabinet 100. As shown in FIG. 1, the testing system 10 further includes a first volatile organic compound (VOC) sensor 124, a first pressure sensor 125, a first carbon dioxide sensor 126, a calibration light source 127, a first humidity sensor 128, and a first temperature sensor 130.

Figure 2:
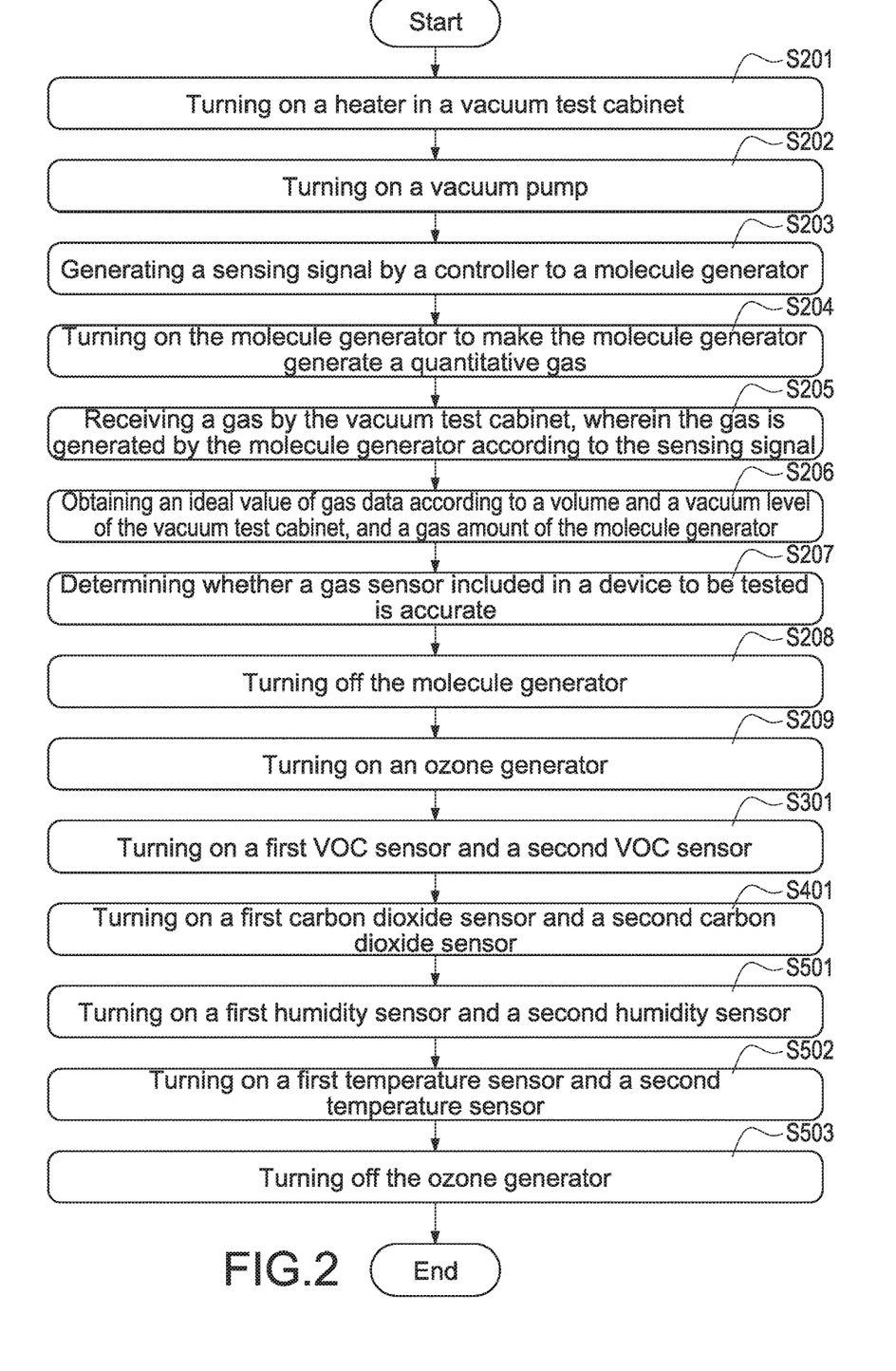
FIG. 2 is a flowchart of a testing method for the air sensing device according to an embodiment of the present invention.

Please refer to FIG. 1, and refer also to FIG. 2, which shows a flowchart of a testing method for the air sensing device according to an embodiment of the present invention. The steps of the test method shown in FIG. 2 are performed by the testing system 10 shown in FIG. 1. The testing method includes the following steps:

Before the test is started, at least one air sensing device 20 to be tested is put in the vacuum test cabinet 100. The air sensing device 20 to be tested includes a gas sensor 202 (a PM2.5 sensor here for example, but not limited), a second VOC sensor 204, a second pressure sensor 205, a second carbon dioxide sensor 206, a second humidity sensor 208, a second temperature sensor 210 and a light sensor 212. The testing system of the air sensing device of the present invention performs the following steps:

Step S201: turning on at least one heater 101 in a vacuum test cabinet 100. When the test is started, an air sensing device 20 to be tested is put in the vacuum test cabinet 100. The controller 110 of the testing system 10 may control the vacuum pump 105 to create a vacuum environment. If a high vacuum environment is needed, the controller 110 of the testing system 10 may control the heater 101 to pre-heat for a period of time (such as one hour) before a predetermined vacuum level is created.

Step S202: turning on a vacuum pump 105. The vacuum pump 105 is connected to the vacuum test cabinet 100 for extracting air from the vacuum test cabinet 100.

Step S203: generating a sensing signal Vs by the controller 110 to the molecule generator 103 when the vacuum level of the vacuum test cabinet 100 meets the required value and then controlling the molecule generator 103 to generate a quantitative gas (such as a pure gas or a mixed gas). More specifically, step S203 further includes: using a first pressure sensor 125 (located in the vacuum test cabinet 100) of the testing system 10 to measure a pressure of the vacuum test cabinet 100, wherein the first pressure sensor 125 is connected to the controller 110 in a wired or wireless manner for the controller 110 determining whether the vacuum level of the vacuum test cabinet 100 meets the required value. Moreover, a calibration light source 127 (located in the vacuum test cabinet 100) of the testing system 10 may also be used in step S203 to control illumination in the vacuum test cabinet 100 for reference by detection afterward.

Step S204: turning on the molecule generator 103 to make the molecule generator 103 generate a quantitative gas (such as a pure gas or a mixed gas) according to the sensing signal Vs of the controller 110.

Step S205: receiving the gas by the vacuum test cabinet 100, wherein the gas is generated by the molecule generator 103 according to the sensing signal Vs. After the molecule generator 103 generates a qualitative gas (such as O2, N2, or CO2) and the quantitative gas according to the sensing signal Vs, a gas sensor 202 (a PM2.5 sensor here for example, but not limited) included in the device 20 to be tested may obtain a measure value of gas data. The controller 110 may perform step S206: obtaining an ideal value of the gas data (also called a system value of the gas data) according to a volume of the vacuum test cabinet 100, the vacuum level of the vacuum test cabinet 100, and the gas amount (controlled by the sensing signal Vs) of the molecule generator 103.

Step S207: determining whether the gas sensor 202 included in the device 20 to be tested is accurate by the controller 110. As shown in FIG. 1, after the device 20 to be tested is put in the vacuum test cabinet 100, the device 20 may be connected to the controller 110 in a wired or wireless manner so that the controller 110 may obtain measure data of the device 20 to be tested. In the step, the controller 110 may obtain a measure value of the gas data of the gas sensor 202 of the air sensing device 20 to be tested and compare the measure value of the gas data with the ideal value of the gas data calculated by the controller 110 in order to determine whether the gas sensor 202 included in the air sensing device 20 to be tested is accurate. Besides, the controller 110 may preset the ideal value of the gas data, calculate the required gas amount according to the volume of the vacuum test cabinet 100 and the vacuum level obtained in step S203, and then generate the required sensing signal Vs. The controller 110 transmits the sensing signal Vs to the molecule generator 103 in step S203 for generating the required gas amount so as to achieve the ideal value of the gas data in the vacuum test cabinet 100.

Step S208: turning off the molecule generator 103. After step S207 is completed, the molecule generator 103 may be turned off to stop generating gas for avoiding influence to measurement afterward.

Step S209: turning on the ozone generator 102. After measurement of the gas amount in the vacuum test cabinet 100 is completed, the testing system 10 may immediately perform the VOC sensing to determine whether the second VOC sensor 204 of the air sensing device 20 to be tested is accurate. According to an embodiment of the present invention, before step S209, the controller 110 of the testing system 10 may first obtain a VOC amount sensed by the first VOC sensor 124 of the testing system 10, and the VOC amount may thus be used as a system value of VOC amount data. Afterward, the controller 110 compares the system value of the VOC amount data with a measure value of the VOC amount data sensed by the second VOC sensor 204 of the air sensing device 20 to be tested for determining whether the second VOC sensor 204 of the air sensing device 20 to be tested is accurate. According to another embodiment of the present invention, step S209 may be omitted and the ozone generator 102 may be turned on directly. The ozone generated by the ozone generator 102 may react with the VOC gas in the vacuum test cabinet 100 and may decrease the VOC gas amount in the vacuum test cabinet 100.

Step S301: turning on the first VOC sensor 124 and the second VOC sensor 204 to measure the VOC gas amount, wherein the VOC gas amount is processed by an ozone treatment in the vacuum test cabinet 100. Qualitatively speaking, after the ozone treatment, the VOC gas amount in the vacuum test cabinet 100 may be decreased. The controller 110 of the testing system 10 may keep monitoring a measure value of the VOC amount data of the second VOC sensor 204 of the air sensing device 20 to be tested. Based on the measure value of the VOC amount data of the second VOC sensor 204, the controller 110 may determine whether the VOC gas amount in the vacuum test cabinet 100 has a decreasing trend based on the measurement of the second VOC sensor 204 for the air sensing device 20 to be tested. Besides, quantitatively speaking, the controller 110 of the testing system 10 may keep monitoring the measure value of the VOC amount data of the second VOC sensor 204 of the air sensing device 20 to be tested and compare the measure value of the VOC amount data with a system value of the VOC amount data measured by the first VOC sensor 124 in the vacuum test cabinet 100 so as to determine whether the second VOC sensor 204 of the air sensing device 20 to be tested is accurate for different VOC amounts.

Step S401: turning on a first carbon dioxide sensor 126 and second carbon dioxide sensor 206 for measuring the carbon dioxide amount processed by the ozone treatment. Qualitatively speaking, after the ozone treatment, the carbon dioxide amount in the vacuum test cabinet 100 may be decreased. The controller 110 of the testing system 10 may keep monitoring a measure value of carbon dioxide amount data of the second carbon dioxide sensor 206 of the air sensing device 20 to be tested. Based on the measure value of the carbon dioxide amount data of the second carbon dioxide sensor 206, the controller 110 may determine whether the carbon dioxide amount in the vacuum test cabinet 100 has a decreasing trend based on the measurement of the second carbon dioxide sensor 206 for the air sensing device 20 to be tested. Besides, quantitatively speaking, the controller 110 of the testing system 10 may keep monitoring the measure value of the carbon dioxide amount data of the second carbon dioxide sensor 206 of the air sensing device 20 to be tested and compare the measure value of the carbon dioxide amount data with a system value of the carbon dioxide amount data measured by the first carbon dioxide sensor 126 in the vacuum test cabinet 100 so as to determine whether the second carbon dioxide sensor 206 of the air sensing device 20 to be tested is accurate for different carbon dioxide amounts.

Step S501: generating the pure water molecule by the molecule generator 103, transforming the pure water molecule into the humidity via the fans, and also turning on a first humidity sensor 128 and second humidity sensor 208. After calibrating the second VOC sensor 204 and the second carbon dioxide sensor 206 of the air sensing device 20 to be tested, the controller 110 may turn on the first humidity sensor 128 of the testing system 10 to measure a system value of humidity data of the vacuum test cabinet 100. The controller 110 turns on the second humidity sensor 208 of the air sensing device 20 to be tested to measure a measure value of the humidity data of the vacuum test cabinet 100. After that, the controller 110 may obtain the system value of the humidity data of the first humidity sensor 128 and the measure value of the humidity data of the second humidity sensor 208 so as to determine whether the second humidity sensor 208 of the air sensing device 20 to be tested is accurate.

Step S502: turning on the heater 101 to heat the vacuum test cabinet 100 and also turning on a first temperature sensor 130 and a second temperature sensor 210. After calibrating the second humidity sensor 208 of the air sensing device 20 to be tested, the controller 110 may turn on the first temperature sensor 130 of the testing system 10 to measure a system value of temperature data in the vacuum test cabinet 100. The controller 110 also turns on the second temperature sensor 210 of the air sensing device 20 to be tested to measure a measure value of the temperature data in the vacuum test cabinet 100. After that, the controller 110 may obtain the system value of the temperature data of the first temperature sensor 130 and the measure value of the temperature data of the second temperature sensor 210 so as to determine whether the second temperature sensor 210 of the air sensing device 20 to be tested is accurate.

Step S211: turning off the ozone generator 102, and completing the test.

Figure 3A:
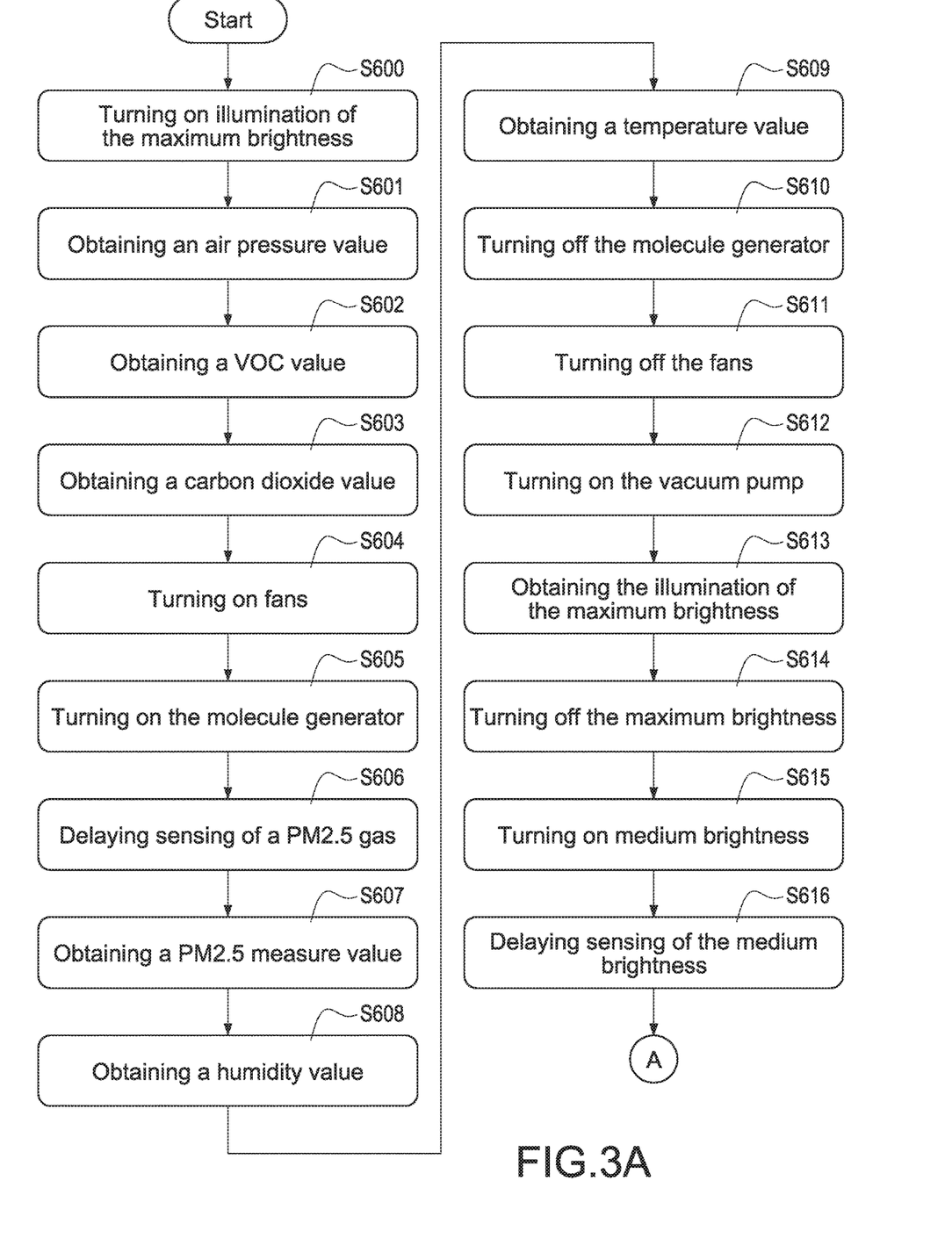
FIG. 3A is a detailed flowchart of a first part of a testing method for the air sensing device according to an embodiment of the present invention.
Figure 3B:
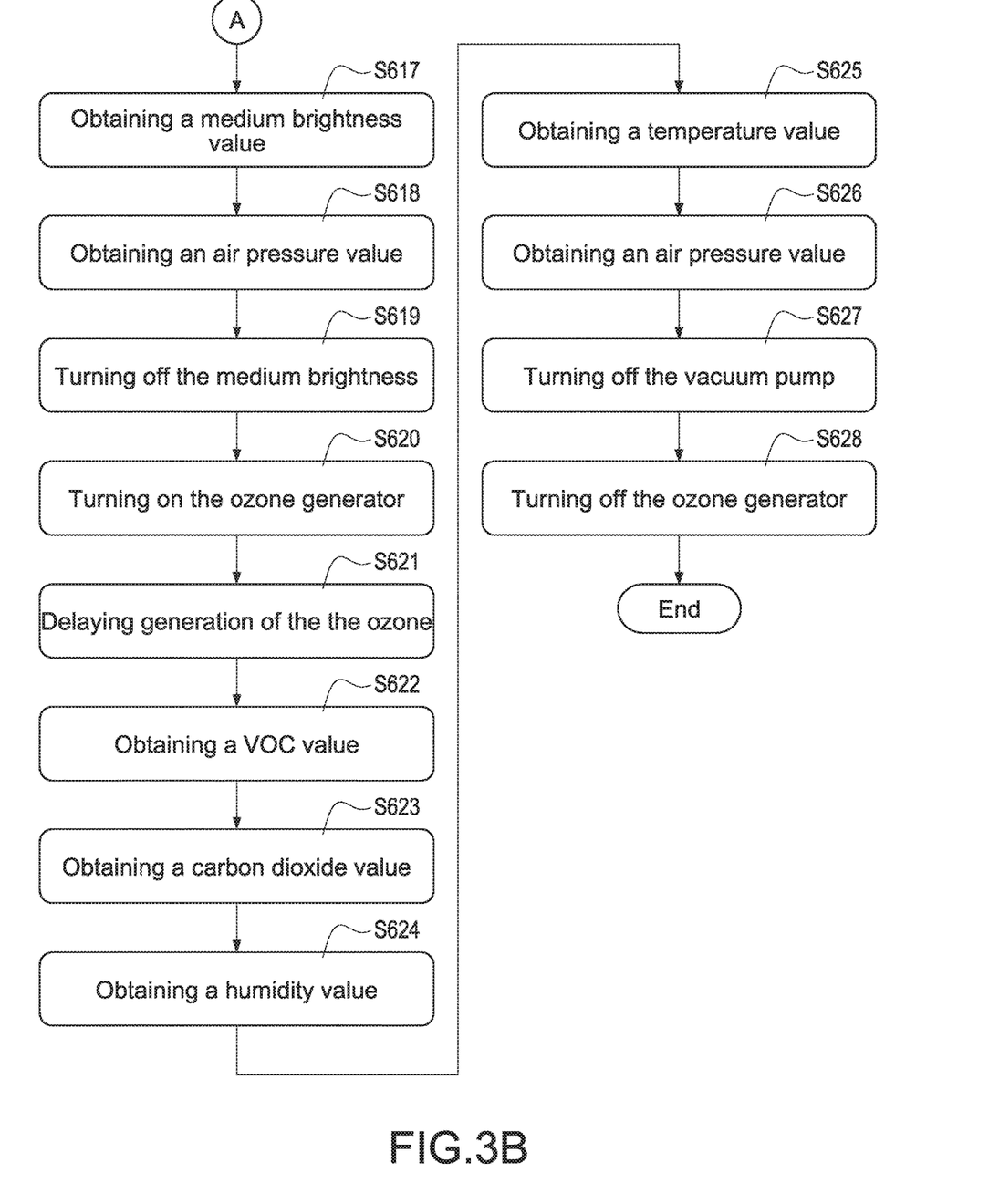
FIG. 3B is a detailed flowchart of a second part following the detailed flowchart of the first part shown in FIG. 3A.

Please refer to FIGS. 3A and 3B. FIG. 3A is a detailed flowchart of a first part of a testing method for the air sensing device according to an embodiment of the present invention and FIG. 3B is a detailed flowchart of a second part following the detailed flowchart of the first part shown in FIG. 3A.

Similarly, before the test starts, at least one air sensing device 20 to be tested is put in the vacuum test cabinet 100. The air sensing device 20 to be tested includes a gas sensor 202 (a PM2.5 sensor here for example, but not limited), a second VOC sensor 204, a second pressure sensor 205, a second carbon dioxide sensor 206, a second humidity sensor 208, a second temperature sensor 210 and a light sensor 212. The testing system of the air sensing device of the present invention performs the following steps:

Step S600: turning on the illumination of the maximum brightness. In step S600, the controller 110 of the testing system 10 may control a calibration light source 127 in the vacuum test cabinet 100 and provide the illumination of the maximum brightness to the vacuum test cabinet 100.

Step S601: obtaining an air pressure value. The controller 110 controls a first pressure sensor 125 in the vacuum test cabinet 100 to obtain an initial air pressure value.

Step S602: obtaining a VOC value. In step S602, the controller 110 controls the first VOC sensor 124 in the vacuum test cabinet 100 to perform measurement for obtaining a system value of VOC amount data. Besides, the controller 110 obtains a measure value of the VOC amount data of the second VOC sensor 204 of the air sensing device 20 to be tested. The controller 110 may compare the system value of the VOC amount data with the measure value of the VOC amount data for determining whether the second VOC sensor 204 of the air sensing device 20 to be tested is accurate.

Step S603: obtaining a carbon dioxide value. In step S603, the controller 110 controls the first carbon dioxide sensor 126 in the vacuum test cabinet 100 to perform measurement for obtaining a system value of the carbon dioxide amount data. Besides, the controller 110 obtains a measure value of the carbon dioxide amount data of the second carbon dioxide sensor 206 of the air sensing device 20 to be tested. The controller 110 may compare the system value of the carbon dioxide amount data with the measure value of the carbon dioxide amount data for determining whether the second carbon dioxide sensor 206 of the air sensing device 20 to be tested is accurate.

Step S604: turning on the fans. The controller 110 turns on the fans to flow the gas.

Step S605: turning on the molecule generator 103. In step S605, the controller 110 generates the sensing signal Vs to the molecule generator 103 for controlling the molecule generator 103 to generate a quantitative gas (such as a pure gas or a mixed gas). The controller 110 may use the air pressure value obtained in step S601, the volume of the vacuum test cabinet 100, the vacuum level of the vacuum test cabinet 100, and the gas amount of the molecule generator 103 (controlled by the sensing signal Vs) so as to obtain an ideal value of gas data (also called as a system value of the gas data).

Step S606: delaying sensing of the PM2.5 gas. The quantitative gas generated by the molecule generator 103 needs a period of time to be spread evenly in the vacuum test cabinet 100. The controller 110 will perform next measurement after a period of delay time when the fans evenly churns the gas.

Step S607: obtaining a PM2.5 measure value. The controller 110 may obtain a measure value of the gas data of a gas sensor 202 of the air sensing device 20 to be tested and compare the measure value of the gas data with the ideal value of the gas data calculated by the controller 110 in step S605 so as to determine whether the gas sensor 202 included in the air sensing device 20 to be tested is accurate.

Step S608: obtaining a humidity value. The controller 110 controls the molecule generator 103 to generate the pure water molecule, transforms the pure water molecule into the humidity via the fans, and also turns on a first humidity sensor 128 of the testing system 10 for measuring a system value of humidity data of the vacuum test cabinet 100. The controller 110 may turn on the first humidity sensor 128 of the testing system 10 to measure a system value of the humidity data of the vacuum test cabinet 100. The controller 110 turns on the second humidity sensor 208 of the air sensing device 20 to be tested to measure a measure value of the humidity data of the vacuum test cabinet 100. After that, the controller 110 may obtain the system value of the humidity data of the first humidity sensor 128 and the measure value of the humidity data of the second humidity sensor 208 so as to determine whether the second humidity sensor 208 of the air sensing device 20 to be tested is accurate.

Step S609: obtaining a temperature value. The controller 110 controls the heater 101 to heat the vacuum test cabinet 100 and also turns on a first temperature sensor 130 of the testing system 10 for measuring a system value of temperature data of the vacuum test cabinet 100. The controller 110 also turns on the second temperature sensor 210 of the air sensing device 20 to be tested to measure a measure value of the temperature data in the vacuum test cabinet 100. After that, the controller 110 may obtain the system value of the temperature data of the first temperature sensor 130 and the measure value of the temperature data of the second temperature sensor 210 so as to determine whether the second temperature sensor 210 of the air sensing device 20 to be tested is accurate.

Step S610: turning off the molecule generator 103. After step S609 is completed, the molecule generator 103 may be turned off to stop generating the gas for avoiding influence to measurement afterward.

Step S611: turning off the fans.

Step S612: turning on a vacuum pump 105. The vacuum pump 105 is connected to the vacuum test cabinet 100 for extracting air from the vacuum test cabinet 100.

Step S613: obtaining the illumination of the maximum brightness. The controller 110 of the testing system 10 may control a calibration light source 127 in the vacuum test cabinet 100 and provide the illumination of the maximum brightness to the vacuum test cabinet 100. Meanwhile, the controller 110 controls the light sensor 212 of the air sensing device 20 to be tested to measure the brightness. The controller 110 obtains the maximum brightness measured by of the light sensor 212 of the air sensing device 20 to be tested for determining whether the light sensor 212 of the air sensing device 20 to be tested is accurate.

Step S614: turning off the maximum brightness. The controller 110 controls the calibration light source 127 in the vacuum test cabinet 100 to turn off the maximum brightness.

Step S615: turning on the medium brightness. The controller 110 of the testing system 10 may control the calibration light source 127 of the vacuum test cabinet 100 and provide the illumination with the medium brightness to the vacuum test cabinet 100.

Step S616: delaying the sensing of the medium brightness.

Step S617: obtaining the medium brightness value. The controller 110 controls the light sensor 212 of the air sensing device 20 to be tested to measure the brightness. The controller 110 obtains the medium brightness value measured by the light sensor 212 of the air sensing device 20 to be tested for determining whether the air sensing device 20 to be tested the light sensor 212 is accurate.

Step S618: obtaining the air pressure value. Since the vacuum pump 105 is turned on in step S612, the controller 110 controls the first pressure sensor 125 in the vacuum test cabinet 100 to keep measuring the air pressure value of the vacuum test cabinet 100 for the controller 110 determining whether the vacuum level of the vacuum test cabinet 100 meets the required value.

Step S619: turning off the medium brightness. After the maximum brightness value and medium brightness value of the light sensor 212 of the air sensing device 20 to be tested are calibrated, a lamp in the vacuum test cabinet 100 can be turned off.

Step S620: turning on the ozone generator. The ozone generated by the ozone generator 102 reacts with the VOC gas in the vacuum test cabinet 100 so that the VOC gas amount and carbon dioxide amount in the vacuum test cabinet 100 may be decreased. The ozone is drawn into the vacuum test cabinet 100, and then dynamical variation of the VOC gas amount and carbon dioxide amount in the vacuum test cabinet 100 may be sensed.

Step S621: delaying the generation of the ozone. Reaction between the ozone and the VOC gas/carbon dioxide in the vacuum test cabinet 100 spends a specific reaction time, thus stopping generating the ozone for a period of time before the VOC gas/carbon dioxide amount is sensed.

Step S622: obtaining the VOC value. Qualitatively speaking, the controller 110 of the testing system 10 may keep monitoring a measure value of VOC amount data of the second VOC sensor 204 of the air sensing device 20 to be tested. Based on the measure value of the VOC amount data of the second VOC sensor 204, the controller 110 may determine whether the VOC gas amount in the vacuum test cabinet 100 has a decreasing trend based on the measurement of the second VOC sensor 204 for the air sensing device 20 to be tested. Besides, quantitatively speaking, the controller 110 of the testing system 10 may keep monitoring the measure value of the VOC amount data of the second VOC sensor 204 of the air sensing device 20 to be tested and compare the measure value of the VOC amount data with a system value of the VOC amount data measured by the first VOC sensor 124 in the vacuum test cabinet 100 so as to determine whether the second VOC sensor 204 of the air sensing device 20 to be tested is accurate for different VOC amounts.

Step S623: obtaining a carbon dioxide value. Qualitatively speaking, the controller 110 of the testing system 10 may keep monitoring a measure value of carbon dioxide amount data of the second carbon dioxide sensor 206 of the air sensing device 20 to be tested. Based on the measure value of the carbon dioxide amount data of the second carbon dioxide sensor 206, the controller 110 may determine whether the carbon dioxide amount in the vacuum test cabinet 100 has a decreasing trend based on the second carbon dioxide sensor 206 for the air sensing device 20 to be tested. Besides, quantitatively speaking, the controller 110 of the testing system 10 may keep monitoring the measure value of the carbon dioxide amount data of the second carbon dioxide sensor 206 of the air sensing device 20 to be tested and compare the measure value of the carbon dioxide amount data with a system value of the carbon dioxide amount data measured by the first carbon dioxide sensor 126 in the vacuum test cabinet 100 so as to determine whether the second carbon dioxide sensor 206 of the air sensing device 20 to be tested is accurate for different carbon dioxide amounts.

Step S624: obtaining a humidity value. Step S624 is similar to the detailed description of step S608, the description thereof is not repeated here.

Step S625: obtaining a temperature value. Step S625 is similar to the detailed description of step S609, the description thereof is not repeated here.

Step S626: obtaining an air pressure value for reference by detection mentioned above.

Step 627: turning off the vacuum pump 105.

Step 628: turning off the ozone generator 102.

Figure 4:
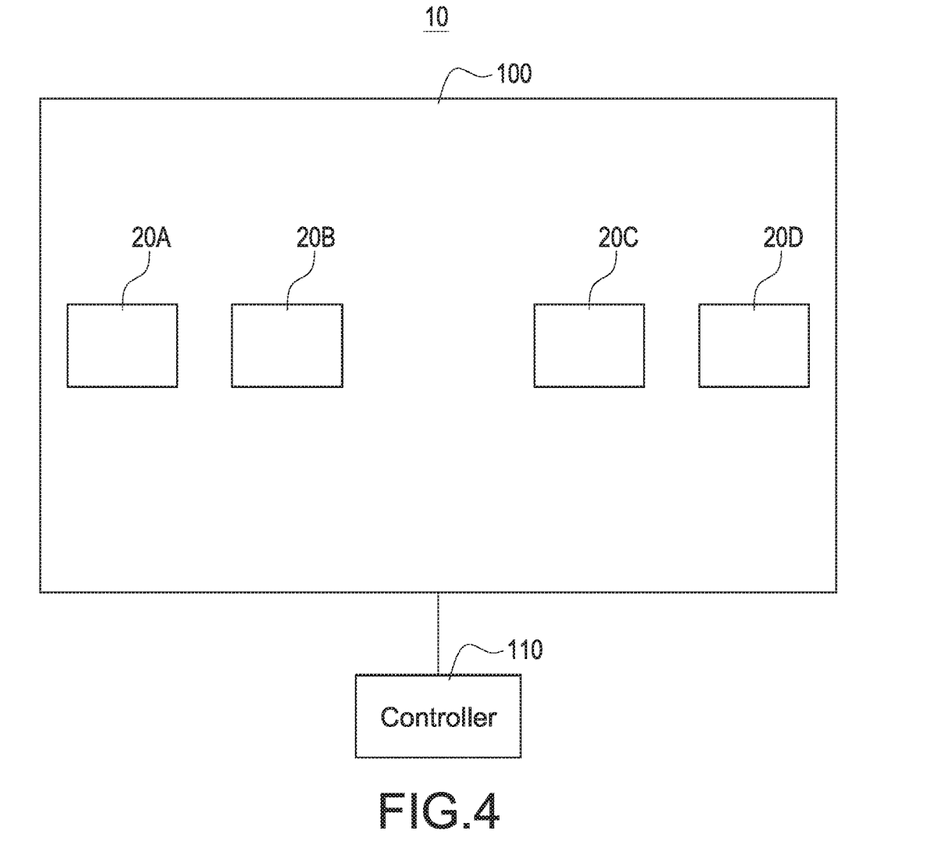
FIG. 4 is a partial block diagram of the testing system for the air sensing device according to an embodiment of the present invention.

Please refer to FIG. 4, which shows a partial block diagram of the testing system for the air sensing device according to an embodiment of the present invention. More than one air sensing devices 20 to be tested may be tested together in the vacuum test cabinet 100. The controller 110 of the testing system 10 may simultaneously perform the steps shown in FIGS. 2, 3A, 3B to the air sensing devices 20 to be tested in order to perform simultaneously qualitative and quantitative tests to gas sensing, VOC sensing, carbon dioxide sensing, humidity sensing, temperature sensing, and brightness sensing of the plurality of air sensing devices 20 to be tested.

Figure 5:
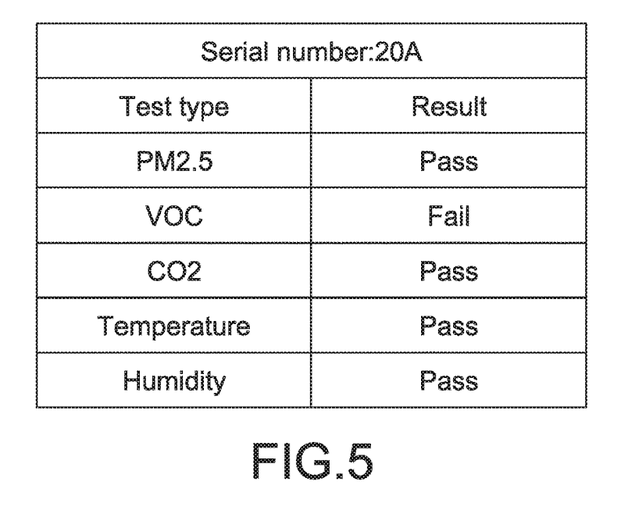
FIG. 5 is a diagram of a testing result of the testing system for the air sensing device according to an embodiment of the present invention.

Please refer to FIG. 5, which shows a diagram of the testing result of a testing system for the air sensing device according to an embodiment of the present invention. Refer also to FIG. 4, when a plurality of air sensing devices 20 to be tested are tested in the vacuum test cabinet 100, the controller 110 of the testing system 10 may obtain a serial number of each of the air sensing devices 20 to be tested and list a test result of each of the air sensing devices 20 to be tested. As shown in FIG. 5, the VOC sensing of the air sensing device 20 with the serial number of 20A is failed, while the rest of the sensing results thereof are passed.

In summary, the present invention provides the testing system and method to switch specific gas to be tested through setting of the vacuum test cabinet, linear pump, and vacuum pump so that the quantitative function is achieved. In addition, specific gas is turned on/off to be tested so that the qualitative function is achieved. Furthermore, an automatic test, automatic determination of test result, automatic recording test result and serial number can be achieved by operations of a computer.

Thus, particular embodiments have been described. Other embodiments are within the scope of the following claims. For example, the actions recited in the claims may be performed in a different order and still achieve desirable results.

What is claimed is:

1. A testing system for an air sensing device, the air sensing device having a gas sensor, the testing system comprising:
   a controller;
   a vacuum test cabinet configured for accommodating the air sensing device;
   a vacuum pump connected to the vacuum test cabinet and the controller; and
   a molecule generator connected to the vacuum test cabinet and the controller;
   wherein the controller is configured to control the vacuum pump to extract air from the vacuum test cabinet so as to create a predetermined vacuum level; the controller is configured to control the molecule generator to generate a quantitative gas and transmit the quantitative gas into the vacuum test cabinet; the controller is configured to obtain a system value of gas data; the controller is configured to obtain a measure value of the gas data of the gas sensor of the air sensing device and compare the measure value of the gas data with the system value of the gas data for determining whether the gas sensor senses correctly.

2. The testing system for the air sensing device of claim 1, wherein the gas sensor is a PM2.5 sensor, the system value of the gas data is a PM2.5 system value of the gas data, and the measure value of the gas data is a PM2.5 measure value of the gas data.

3. The testing system for the air sensing device of claim 2, further comprising:
   an ozone generator connected to the vacuum test cabinet and the controller; and
   a first volatile organic compound (VOC) sensor located in the vacuum test cabinet, and the first VOC sensor connected to the controller;
   the air sensing device further comprising a second VOC sensor;
   wherein the controller is configured to control the ozone generator to generate the ozone and transmit the ozone into the vacuum test cabinet; the controller is configured to control the first VOC sensor in the vacuum test cabinet to detect a system value of VOC amount data; the controller is configured to obtain a measure value of the VOC amount data measured by the second VOC sensor of the air sensing device; the controller is configured to compare the system value of the VOC amount data with the measure value of the VOC amount data for determining whether the second VOC sensor of the air sensing device senses correctly.

4. The testing system for the air sensing device of claim 3, further comprising:
   a first carbon dioxide sensor located in the vacuum test cabinet, and the first carbon dioxide sensor is connected to the controller;
   the air sensing device further comprising a second carbon dioxide sensor;
   wherein the controller is configured to control the ozone generator to generate the ozone and transmit the ozone into the vacuum test cabinet; the controller is configured to control the first carbon dioxide sensor in the vacuum test cabinet to detect a system value of carbon dioxide amount data; the controller is configured to obtain a measure value of the carbon dioxide amount data measured by the second carbon dioxide sensor of the air sensing device; the controller is configured to compare the system value of the carbon dioxide amount data with the measure value of the carbon dioxide amount data for determining whether the second carbon dioxide sensor of the air sensing device senses correctly.

5. The testing system for the air sensing device of claim 2, wherein the controller is configured to obtain the PM2.5 system value of the gas data according to a vacuum level, a volume of the vacuum test cabinet, and a gas amount of the molecule generator.

6. The testing system for the air sensing device of claim 1, further comprising:
   a linear valve connected between the ozone generator and the vacuum test cabinet.

7. The testing system for the air sensing device of claim 1, further comprising:
   a first humidity sensor located in the vacuum test cabinet, and the first humidity sensor connected to the controller;
   the air sensing device further comprising a second humidity sensor;
   wherein the controller is configured to control the first humidity sensor in the vacuum test cabinet to detect a system value of humidity data; the controller is configured to obtain a measure value of the humidity data measured by the second humidity sensor of the air sensing device; the controller is configured to compare the system value of the humidity data with the measure value of the humidity data for determining whether the second humidity sensor of the air sensing device senses correctly.

8. The testing system for the air sensing device of claim 1, further comprising:
a first temperature sensor located in the vacuum test cabinet, and the first temperature sensor connected to the controller;
the air sensing device further comprising a second temperature sensor;
wherein the controller is configured to control the first temperature sensor in the vacuum test cabinet to detect a system value of temperature data; the controller is configured to obtain a measure value of the temperature data measured by the second temperature sensor of the air sensing device; the controller is configured to compare the system value of the temperature data with the measure value of the temperature data for determining whether the second temperature sensor of the air sensing device senses correctly.

9. The testing system for the air sensing device of claim 1, wherein the vacuum test cabinet further comprises a heater, and the controller is configured to control the heater to pre-heat for a predetermined time before the predetermined vacuum level is created.

10. A testing method for an air sensing device having a gas sensor, the testing method comprising the following steps of:
(a) arranging at least one air sensing device in a vacuum test cabinet;
(b) controlling a vacuum pump by a controller to extract air from the vacuum test cabinet for creating a predetermined vacuum level;
(c) controlling a molecule generator by the controller to generate a quantitative gas and transmit the quantitative gas into the vacuum test cabinet for the controller obtaining a system value of gas data; and
(d) obtaining a measure value of the gas data of the gas sensor of the air sensing device and comparing the measure value of the gas data with the system value of the gas data by the controller for determining whether the gas sensor senses correctly.

11. The testing method for the air sensing device of claim 10, wherein the gas sensor is a PM2.5 sensor, the system value of the gas data is a PM2.5 system value of the gas data, and the measure value of the gas data is a PM2.5 measure value of the gas data.

12. The testing method for the air sensing device of claim 11, wherein in step (c), the controller is configured to obtain the PM2.5 system value of the gas data according to a vacuum level, a volume of the vacuum test cabinet, and a gas amount of the molecule generator.

13. The testing method for the air sensing device of claim 11, further comprising the following steps of:
(e) controlling an ozone generator by the controller to generate the ozone and transmit the ozone into the vacuum test cabinet;
(f1) controlling a first volatile organic compound (VOC) sensor in the vacuum test cabinet by the controller to detect a system value of VOC amount data;
(f2) obtaining a measure value of the VOC amount data by the controller, wherein the measure value of the VOC amount data is measured by a second VOC sensor of the air sensing device; and
(f3) comparing the system value of the VOC amount data with the measure value of the VOC amount data by the controller for determining whether the second VOC sensor of the air sensing device senses correctly.

14. The testing method for the air sensing device of claim 13, wherein after step (e) the testing method further comprises the following steps of:
(g1) controlling a first carbon dioxide sensor in the vacuum test cabinet by the controller to detect a system value of carbon dioxide amount data;
(g2) obtaining a measure value of the carbon dioxide amount data by the controller, wherein the measure value of the carbon dioxide amount data is measured by a second carbon dioxide sensor of the air sensing device; and
(g3) comparing the system value of the carbon dioxide amount data with the measure value of the carbon dioxide amount data by the controller for determining whether the second carbon dioxide sensor of the air sensing device senses correctly.

15. The testing method for the air sensing device of claim 10, further comprising the following steps of:
(h1) controlling a first temperature sensor in the vacuum test cabinet by the controller to detect a system value of temperature data;
(h2) obtaining a measure value of the temperature data by the controller, wherein the measure value of the temperature data is measured by a second temperature sensor of the air sensing device; and
(h3) comparing the system value of the temperature data with the measure value of the temperature data by the controller for determining whether the second temperature sensor of the air sensing device senses correctly.

16. The testing method for the air sensing device of claim 10, further comprising the following steps of:
(j1) controlling a first humidity sensor in the vacuum test cabinet by the controller to detect a system value of the humidity data;
(j2) obtaining a measure value of the humidity data by the controller, wherein the measure value of the humidity data is measured by a second humidity sensor of the air sensing device; and
(j3) comparing the system value of the humidity data with the measure value of the humidity data by the controller for determining whether the second humidity sensor of the air sensing device senses correctly.

17. The testing method for the air sensing device of claim 10, wherein after step (a) the testing method further comprises the following step of:
(a1) controlling a heater by the controller to pre-heat for a predetermined time.

* * * * *